United States Patent [19]

Geering

[11] Patent Number: 4,649,209

[45] Date of Patent: Mar. 10, 1987

[54] PROCESS FOR PREPARING METHYL CHLOROSULFATES

[75] Inventor: Emil J. Geering, Grand Island, N.Y.

[73] Assignee: Occidental Chemical Corporation, Niagara Falls, N.Y.

[21] Appl. No.: 762,178

[22] Filed: Aug. 5, 1985

[51] Int. Cl.$^4$ .................................... C07C 143/68
[52] U.S. Cl. ........................................ 558/46; 558/54
[58] Field of Search ............... 260/456 R; 558/46, 54

[56] References Cited

PUBLICATIONS

Buncel, *Chemical Reviews,* Chlorosulfates, vol. 70, pp. 323–327 (1970).

Binderup et al., *Synthetic Comm.,* 14(a), pp. 857–864 (1984).

*Primary Examiner*—Nicky Chan
*Attorney, Agent, or Firm*—James F. Tao; William G. Gosz

[57] ABSTRACT

A process for preparing methyl chlorosulfates by reacting methylene chloride with sulfur trioxide, stabilizing and distilling the reaction mixture, and recovering at least one methyl chlorosulfate as a distillate is disclosed. Preferably, the reaction produces two methyl chlorosulfates, i.e. chloromethyl chlorosulfate and methylene bis-(chlorosulfate), which are separated and recovered by fractional distillation.

8 Claims, No Drawings

PROCESS FOR PREPARING METHYL CHLOROSULFATES

BACKGROUND OF THE INVENTION

This invention relates to an improved process for preparing methyl chlorosulfates by reacting methylene chloride with sulfur trioxide. This process is more efficient and cost effective as compared to those processes in current use.

Alkyl chlorosulfates, such as methyl chlorosulfates, have a variety of practical uses and are of current industrial interest and importance. These compounds are used extensively in organic synthesis where they are employed as intermediates in the synthesis of alkyl hydrogen sulfates, particularly long chain alcohols. Alkyl hydrogen sulfates are in turn useful as detergents builders. Alkyl chlorosulfates are also useful as alkylating agents and as chemical intermediates. See generally, E. Buncel, *Chemical Reviews,* Volume 70, page 323 (1970).

Recently, it has been discovered that certain alkyl chlorosulfates are useful reagents for the synthesis of chloromethyl esters of certain B-lactam antibiotics, such as penicillin acid sulfone. Chloromethyl chlorosulfate is particularly useful in such esterification reactions due to the mild reaction conditions, short reaction time and high yields which are achievable. In addition, bis(acyloxy) methanes are conveniently prepared using methylene bis(chlorosulfate). See E. Binderup and E. T. Hansen, *Synthetic Communications,* 14(9), pages 857 to 864 (1984).

Recently, it has been proposed to employ methylene bis(chlorosulfate) as an electrolyte in lithium batteries. Lithium batteries are of current interest for both military and commercial applications since they are capable of developing much higher voltages than other storage batteries of comparable size. Presently, thionyl chloride is used as the electrolyte of choice in lithium batteries. However, thionyl chloride has a relatively low vapor pressure which can cause the batteries to develop excessive pressure resulting in leakage of electrolyte from the battery container and failure of the battery. A nonvolatile electrolyte having properties similar or superior to thionyl chloride would obviously represent an advance in this art.

Although the demand for methyl chlorosulfates has increased in recent years, the current technology for manufacturing such products is still relatively inefficient. Among the processes disclosed in the prior art are the reaction of alcohols with sulfuryl chloride, the reaction of alkyl sulfites with chlorine, and the alkylation of chlorosulfonic acid. These processes are summarized in E. Buncel, *Chemical Reviews, supra.* The reaction of chlorosulfonic acid with bromochloromethane to prepare chloromethyl chlorosulfate is also described in E. Binderup and E. T. Hansen, *Synthetic Communications, supra.*

The reaction of sulfur trioxide with either ethyl chloride or ethyl chloroformate to prepare ethyl chlorosulfate has also been reported. Similarly, sulfur trioxide can react with 1,2-dichloroethane to yield the chlorosulfate $ClCH_2CH_2OSO_2Cl$. However, the reported yields for these reactions are not high. See *Chemical Reviews, supra.*

It is therefore a principle object of the present invention to provide an improved process for preparing methyl chlorosulfates which is more efficient and cost effective than known processes.

SUMMARY OF THE INVENTION

In accordance with the present invention, an improved process for preparing methyl chlorosulfates comprises the steps of
 (a) reacting methylene chloride with sulfur trioxide,
 (b) adding a stabilizing agent to the reaction mixture,
 (c) distilling the stabilized reaction mixture, and
 (d) recovering at least one methyl chlorosulfate as a distillate.

Preferably, the stabilizing agent is sodium carbonate or sodium bicarbonate, or mixtures thereof, and both chloromethyl chlorosulfate and methylene bis(chlorosulfate) are recovered from the reaction mixture by fractional distillation. Methylene bis(chlorosulfate) is believed to be a novel compound.

DETAILED DESCRIPTION OF THE INVENTION

Although the process of this invention can be used to advantage to prepare a variety of methyl chlorosulfates as will be readily appreciated by those skilled in the art, it is particularly adpated to preparing chloromethyl chlorosulfate ($ClCH_2OSO_2Cl$) and methylene bis(chlorosulfate) ($CH_2(OSO_2Cl)_2$). These compounds are both produced by the reaction of methylene chloride with sulfur trioxide as shown below:

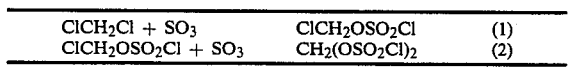

| | | |
|---|---|---|
| $ClCH_2Cl + SO_3$ | $ClCH_2OSO_2Cl$ | (1) |
| $ClCH_2OSO_2Cl + SO_3$ | $CH_2(OSO_2Cl)_2$ | (2) |

The production of chloromethyl chlorosulfate and methylene bis(chlorosulfate) as depicted above results from the two sequential reactions (1) and (2). In practice, however, reactions (1) and (2) are not discrete and some quantity of both chloromethyl chlorosulfate and methylene bis(chlorosulfate) is normally present in the reaction mixture. Thus, at sulfur trioxide to methylene chloride mole ratios of as low as 0.5 or less, a significant amount of chloromethyl chlorosulfate is present in the reaction mixture. As the sulfur trioxide to methylene chloride mole ratio is increased, methylene bis(chlorosulfate) is present in the reaction mixture in increasing amounts. If both products are desired, optimal results are obtained at mole ratios in the range of from about 0.5 to about 2.5. Since the products have different boiling points, they can be conveniently separated by fractional distillation. Alternatively, mole ratios of sulfur trioxide to methylene chloride of more than about 2.5 can be used to prepare methylene bis(chlorosulfate) as the sole reaction product.

It is preferred to add the desired amount of sulfur trioxide to a well-stirred reaction vessel containing the methylene chloride until the reaction is substantially complete. The reaction is slightly exothermic and can be controlled by cooling the reaction vessel to the desired temperature. A temperature in the range of from about 0° C. to about 50° C. is preferred.

Prior to distillation, it is necessary to add a stabilizing agent to the reaction mixture. The stabilizing agent prevents decomposition of the reaction mixture which would occur normally upon distillation. The reason for the decomposition is not perfectly understood, but is believed to be caused by unstable acidic components in the reaction mixture. Suitable stabilizing agents for purposes of the present invention include sodium carbonate and sodium bicarbonate. The use of a stabilizing agent permits distillation without substantial decomposition at distillation temperatures as high as 100° C. Distillation temperatures in the range of from about 50° C. to about 100° C. are generally suitable. Preferably, the stabilizing agent is present in an amount of from about 5% to about 10% by weight of the reaction mixture.

After the addition of a stabilizing agent to the reaction mixture, the mixture is filtered to remove solids and the filtrate is distilled to separate the reaction products. When both chloromethyl chlorosulfate and methylene bis(chlorosulfate) are present in the filtrate, a two-stage fractional distillation procedure is used. The first stage of the distillation is preferably conducted at a temperature of from about 50° to about 60° C. and yields chloromethyl chlorosulfate as the primary product. The second-stage distillation is preferably conducted at a temperature of from about 85° C. to about 95° C. and yields methylene bis(chlorosulfate) as the primary product.

The methyl chlorosulfates of the present invention have a variety of practical uses of industrial importance as mentioned previously. Methylene bis(chlorosulfate) is currently being evaluated as an electrolyte for lithium batteries. In this application, a high purity product is desirable. Therefore, the product must undergo substantial purification after recovery from the reaction described above prior to its use as a battery electrolyte. Since methylene bis(chlorosulfate) boils at about 100° C., it is much less volatile than thionyl chloride which is presently used as an electrolyte in lithium batteries, and therefore it is less subject to leakage from the battery container and subsequent failure of the battery when in service. This is particularly important in military applications where survivability and reliability of electronic systems is critical.

The following example is intended to illustrate various embodiments and advantages of the present invention without limiting it thereby.

EXAMPLE

A closed, desiccated system consisting of a reaction flask equipped with a stirrer, a pressure-equalizing addition funnel and a thermometer was prepared. Six moles (480 grams) of sulfur trioxide was added, during 65 minutes, to six moles (510 grams) of well-stirred methylene chloride. The slight exotherm was controlled and the temperature of the mixture was held to 25 to 28 degrees Centigrade by suspending the reaction flask over dry ice chunks in a Dewar flask. Ten minutes after the completion of the addition 20 grams of sodium carbonate was added to the stirred reaction mixture. The slurry was stirred for one hour. 47 Grams of sodium bicarbonate was then added and the slurry stirred for ten minutes. The mixture was filtered, under anhydrous conditions, through a fritted glass filter to give 898 grams of filtrate.

The filtrate was fractionated in a two-part distillation. In the first part, the more-volatile portion was distilled through a 14" vacuum-jacketed Vigreux column. A 369 gram fraction was collected at a temperature of 55 to 58 degrees Centigrade at 18 mm of pressure. The column was then removed and the residue was distilled up-and-over to give a 363 gram fraction at 88 to 92 degrees Centigrade at about 0.1 mm.

The first fraction was analyzed by infra red and nmr spectra and found to be chloromethyl chlorosulfate. It was collected in 37.3% yield. The second fraction, methylene bis(chlorosulfate), also identified by infra red and nmr, was obtained in 49.3% yield. The combined distilled and collected yield was 86.6%.

What is claimed is:

1. A process for preparing at least one methyl chlorosulfate comprises the steps of:
    (a) reacting methylene chloride with sulfur trioxide,
    (b) adding a stabilizing agent selected from the group consisting of sodium carbonate, sodium bicarbonate, and mixtures thereof to the reaction mixture,
    (c) distilling the stabilized reaction mixture, and
    (d) recovering at least one methyl chlorosulfate selected from the group consisting of chloromethyl chlorosulfate and methylene bis(chlorosulfate) as a distillate.

2. The process of claim 1 wherein the reaction is conducted at a temperature of from about 0° C. to about 50° C.

3. The process of claim 1 wherein the mole ration of sulfur trioxide to methylene chloride is from about 0.5 to about 2.5.

4. The process of claim 1 wherein the mole ratio of sulfur trioxide to methylene chloride is more than about 2.5.

5. The process of claim 5 wherein methylene bis(chlorosulfate) is recovered as a distillate.

6. The process of claim 1 wherein the stabilizing agent is present in an amount of from about 5% to about 10% by weight of the reaction mixture.

7. The process of claim 1 wherein the distillation is conducted at a temperature of from about 50° C. to about 100° C.

8. The process of claim 7 wherein the distillation is a two-stage fractional distillation, the first stage being conducted at a temperature of from about 50° C. to about 60° C., and the second stage being conducted at a temperature of from about 85° C. to about 95° C.

* * * * *

Disclaimer 4,649,209.—*Emil J. Geering*, Grand Island, N. Y. PROCESS FOR PREPARING METHYL CHLOROSULFATES. Patent dated Mar. 10, 1987. Disclaimer filed Aug. 25, 1989, by the assignee, Occidental Chemical Corporation.

Hereby enters this disclaimer to the entire term of said patent.
[*Official Gazette November 21, 1989*]